United States Patent [19]
Hawkins

[11] Patent Number: 6,013,805
[45] Date of Patent: Jan. 11, 2000

[54] PENTAFLUOROTHIO-SUBSTITUTED ISOXAZOLES

[75] Inventor: David William Hawkins, Ongar, United Kingdom

[73] Assignee: Rhone-Poulenc Agriculture Ltd, Ongar, United Kingdom

[21] Appl. No.: 09/162,062

[22] Filed: Sep. 29, 1998

Related U.S. Application Data

[62] Division of application No. 08/822,926, Mar. 21, 1997, Pat. No. 5,849,928.

[30] Foreign Application Priority Data

Mar. 22, 1996 [GB] United Kingdom ............... 9606015

[51] Int. Cl.[7] ............... C07D 261/08; C07D 261/18; C07D 261/10; A01N 43/80; A01N 41/40; C07C 317/114
[52] U.S. Cl. ............... 548/248; 504/271; 504/309; 548/243; 548/245; 564/405
[58] Field of Search ............... 548/248, 243, 548/245; 504/271, 309; 564/405

[56] References Cited

U.S. PATENT DOCUMENTS

| 5,656,573 | 8/1997 | Roberts et al. | 504/271 |
| 5,849,928 | 12/1998 | Hawkins | 548/248 |

FOREIGN PATENT DOCUMENTS

| 0213892 | 3/1987 | European Pat. Off. |
| 0418175 | 3/1991 | European Pat. Off. |
| 0487357 | 5/1992 | European Pat. Off. |
| 0496630 | 7/1992 | European Pat. Off. |
| 0496631 | 7/1992 | European Pat. Off. |
| 0524018 | 1/1993 | European Pat. Off. |
| 0527036 | 2/1993 | European Pat. Off. |
| 0527037 | 2/1993 | European Pat. Off. |
| 0560482 | 9/1993 | European Pat. Off. |
| 0560483 | 9/1993 | European Pat. Off. |
| 0625505 | 11/1994 | European Pat. Off. |
| 0625508 | 11/1994 | European Pat. Off. |
| 2276379 | 9/1994 | United Kingdom. |
| 2276380 | 9/1994 | United Kingdom. |
| 2276381 | 9/1994 | United Kingdom. |
| 2276382 | 9/1994 | United Kingdom. |
| 95/25099 | 9/1995 | WIPO. |
| 97/05106 | 2/1997 | WIPO. |

OTHER PUBLICATIONS

Sheppard, *J. Am. Chem. Soc.*, 84, pp. 3064–3072 (1962).

*Primary Examiner*—Floyd D. Higel
*Attorney, Agent, or Firm*—Burns, Doane, Swecker & Mathis, L.L.P.

[57] ABSTRACT

The invention relates to intermediates to herbicidal compounds of formulae (Ia), (Ib) or (Ic):

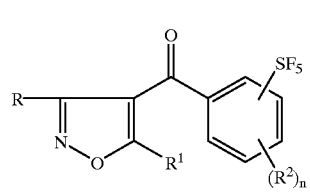

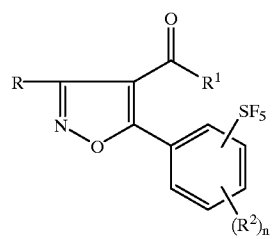

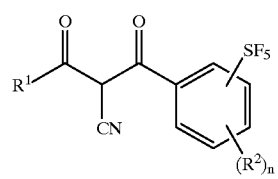

9 Claims, No Drawings

PENTAFLUOROTHIO-SUBSTITUTED ISOXAZOLES

This application is a divisional of U.S. patent application Ser. No. 08/822,926, filed Mar. 21, 1997, now U.S. Pat. No. 5,849,928, which is incorporated by reference herein in its entirety and relied upon.

BACKGROUND OF THE INVENTION

1. Field of the Invention

This invention relates to novel isoxazole derivatives and 2-cyano-1,3-dione derivatives, compositions containing them, processes for their preparation, intermediates in their preparation and their use as herbicides.

2. Description of the Background Art

Herbicidal 4-benzoylisoxazoles are described in European Patent Publication Numbers 0418175, 0487357, 0527036, 0527037, 0560482 and 0560483. Herbicidal 2-cyano-1,3-diones are described in European Patent Publication Numbers 0213892, 0496630, 0496631, 0625505 and 0625508, and International Patent Publication No. WO 95/25099. Herbicidal 5-phenylisoxazoles are described in European Patent Publication Number 0524018. However, none of the above publications disclose or suggest the presence of a pentafluorosulphanyl group as a substituent on the phenyl ring.

SUMMARY OF THE INVENTION

The present invention provides 4-benzoylisoxazole derivatives of formula (Ia), 5-phenylisoxazole derivatives of formula (Ib) and 2-cyano-1,3-dione derivatives of formula (Ic):

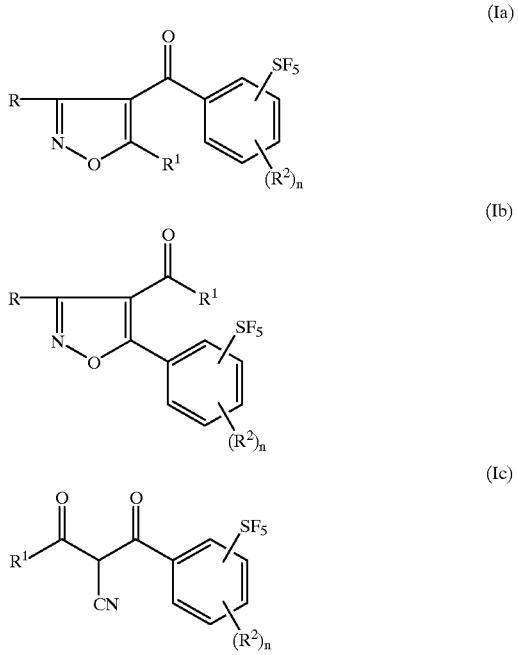

wherein:

R represents hydrogen or —$CO_2R^3$;

$R^1$ represents:

a straight- or branched- chain alkyl group containing up to six carbon atoms which is optionally substituted by one or more halogen atoms; or a cycloalkyl group containing from three to six ring carbon atoms optionally substituted by one or more groups selected from $R^4$ and halogen;

$R^2$ represents:

halogen;

a straight- or branched- chain alkyl group containing up to six carbon atoms which is substituted by one or more groups —$OR^5$;

a cycloalkyl group containing from three to six carbon atoms; or a group selected from nitro, cyano, —$CO_2R^5$, —$NR^5R^6$, —$S(O)_pR^7$, —$O(CH_2)_mOR^5$, —$COR^5$, —$N(R^8)SO_2R^7$, —$OR^7$, —$OH$, —$OSO_2R^7$, —$(CR^9R^{10})SO_qR^{7a}$, —$CONR^5R^6$, —$N(R^8)$—$C(Z)=Y$, —$(CR^9R^{10})NR^8R^{11}$ and $R^4$;

n represents zero or an integer from one to three; where n is greater than one the groups $R^2$ may be the same or different;

m represents one, two or three;

p represents zero, one or two;

q represents zero, one or two;

t represents an integer from one to four (preferably one);

$R^3$ represents a straight- or branched- chain alkyl group containing up to six carbon atoms optionally substituted by one or more groups selected from halogen, —$OR^5$, —$CO_2RS$, —$S(O)_pR^7$, phenyl or cyano; or phenyl optionally substituted by one or more groups selected from halogen, —$OR^5$ and $R^4$;

$R^4$ represents a straight- or branched- chain alkyl, alkenyl or alkynyl group containing up to six carbon atoms optionally substituted by one or more halogen atoms;

$R^5$ and $R^6$ which may be the same or different, each represents hydrogen or $R^4$;

$R^7$ and $R^{7a}$ independently represent $R^4$ or a cycloalkyl group containing from three to six ring carbon atoms; or a group —$(CH_2)_w$-[phenyl optionally substituted by from one to five groups $R^{12}$ which may be the same or different];

w represents zero or one;

$R^8$ represents:

hydrogen;

a straight- or branched- chain alkyl, alkenyl or alkynyl group containing up to ten carbon atoms optionally substituted by one or more halogen atoms;

a cycloalkyl group containing from three to six ring carbon atoms;

—$(CH_2)_w$-[phenyl optionally substituted by from one to five groups $R^{12}$ which may be the same or different]; or a group —$OR^{13}$;

$R^9$ and $R^{10}$ independently represent hydrogen or a straight- or branched- chain alkyl group containing up to six (preferably up to three) carbon atoms optionally substituted by one or more halogen atoms;

$R^{11}$ represents —$S(O)_qR^7$ or —$C(Z)=Y$;

$R^{12}$ represents:

a halogen atom;

a straight- or branched- chain alkyl group containing up to three carbon atoms optionally substituted by one or more halogen atoms;

or a group selected from nitro, cyano, —$S(O)_pR^3$ and —$OR^5$;

Y represents oxygen or sulphur (preferably Y represents oxygen);

Z represents $R^4$, —$NR^8R^{13}$, —$NR^8$—$NR^{13}R^{14}$, —$SR^7$ or —$OR^7$;

$R^{13}$ and $R^{14}$ independently represent $R^8$;

and agriculturally acceptable salts and metal complexes thereof, which possess valuable herbicidal properties.

Compounds of formula (Ic) may exist in enolic tautomeric forms that may give rise to geometric isomers around the enolic double bond. It will also be appreciated that certain substituents in the compounds of the invention may contribute to optical isomerism and/or stereoisomerism. All such forms are embraced by the present invention.

DETAILED DESCRIPTION OF THE INVENTION AND PREFERRED EMBODIMENTS

It will be understood that in the description that follows, reference to compounds of formula (I) means reference to compounds of formula (Ia), (Ib) or (Ic).

By the term "pentafluorosulphanyl" is meant a radical of the formula —$SF_5$, which can also be termed "pentafluorothio".

By the term "agriculturally acceptable salts" is meant salts the cations or anions of which are known and accepted in the art for the formation of salts for agricultural or horticultural use. Preferably the salts are water-soluble. Suitable salts with bases include alkali metal (eg. sodium and potassium), alkaline earth metal (eg. calcium and magnesium), ammonium and amine (eg. diethanolamine, triethanolamine, octylamine, morpholine and dioctylmethylamine) salts. Suitable acid addition salts, formed by compounds of formula (I) containing an amino group, include salts with inorganic acids, for example hydrochlorides, sulphates, phosphates and nitrates and salts with organic acids, for example acetic acid.

By the term "metal complexes" is meant compounds in which one or both of the oxygen atoms of the 1,3-dione of formula (Ic) act as chelating agents to a metal cation. Examples of such cations include zinc, manganese, cupric, cuprous, ferric, ferrous, titanium and aluminium.

Compounds of formula (Ia) are preferred.

Compounds in which the 2-position of the phenyl group is substituted are also preferred.

Preferably the 5- and 6- positions of the phenyl group are unsubstituted.

Preferably $R^1$ represents:

a straight- or branched- chain alkyl group containing up to three carbon atoms which is optionally substituted by one or more halogen atoms; or cyclopropyl or 1-methylcyclopropyl.

Most preferably $R^1$ represents cyclopropyl.

Preferably $R^2$ represents:

halogen;

a straight- or branched- chain alkyl or alkenyl group containing up to four carbon atoms optionally substituted by one or more halogen atoms;

or a group selected from nitro, cyano, —$S(O)_pR^7$, —$OR^7$ and —$CR^9R^{10}SO_qR^7$.

Preferably n represents zero, one or two.

Preferably $R^3$ represents a straight- or branched- chain alkyl group containing up to six carbon atoms optionally substituted by one or more halogen atoms.

Preferably $R^7$ represents a straight- or branched- chain alkyl group containing up to six carbon atoms which is optionally substituted by one or more halogen atoms;

or phenyl optionally substituted by halogen, a straight- or branched- chain alkyl containing up to three carbon atoms optionally substituted by one or more halogen atoms, or —$S(O)_pR^3$.

A particularly preferred class of compounds of formula (Ia) are those having one or more of the following properties:

R represents hydrogen or —$CO_2R^3$;
$R^1$ represents cyclopropyl or 1-methylcyclopropyl;
$R^2$ represents:
halogen;
a straight- or branched- chain alkyl group containing up to three carbon atoms optionally substituted by one or more halogen atoms;
—$S(O)_pR^7$ group;
—$CH_2S(O)_qR^{7a}$;
n represents zero, one or two;
$R^3$ represents a straight- or branched- chain alkyl group containing from one to three carbon atoms;
$R^7$ represents methyl or ethyl optionally substituted by one or more halogen atoms;
$R^{7a}$ represents a straight- or branched-chain alkyl group containing up to four carbon atoms optionally substituted by one or more halogen atoms,or phenyl optionally substituted by one or more halogen atoms or —$S(O)_pR^7$.

Another particularly preferred class of compounds of formula (Ia) are those wherein:
R represents hydrogen, or —$CO_2R^3$;
$R^1$ represents cyclopropyl;
$R^2$ represents:
halogen;
methyl optionally substituted by from one to three halogen atoms (preferably fluorine);
nitro; or —$S(O)_pCH^3$;
n represents zero, one or two; and
$R^3$ represents methyl or ethyl.

Another particularly preferred class of compounds of formula (Ia) are those wherein:
R represents hydrogen;
$R^1$ represents cyclopropyl;
$R^2$ represents:
methyl optionally substituted by from one to three halogen atoms (preferably fluorine);
nitro; or —$S(O)_pCH_3$;
n represents zero, one or two.

Particularly important compounds of formula (I) include the following:

1. 5-cyclopropyl-4-(4-pentafluorosulphanylbenzoyl) isoxazole;
2. 4-cyclopropylcarbonyl-5-(4-pentafluorosulphanylphenyl)isoxazole;
3. 2-cyano-3-cyclopropyl-1-(4-pentafluorosulphanylphenyl)propan-1,3-dione;
4. 5-cyclopropyl-4-(2-nitro-4-pentafluorosulphanylbenzoyl)isoxazole;
5. 5-cyclopropyl-4-(2-methylthio-4-pentafluorosulphanylbenzoyl)isoxazole;
6. 5-cyclopropyl-4-(2-methylsulphinyl-4-pentafluorosulphanylbenzoyl)isoxazole;
7. 5-cyclopropyl-4-(2-methylsulphonyl-4-pentafluorosulphanylbenzoyl)isoxazole;
110. 4-cyclopropylcarbonyl-5-(2-methylthio-4-pentafluorosulphanylphenyl)isoxazole;
111. 2-cyano-3-cyclopropyl-1-(2-nitro-4-pentafluorosulphanylphenyl)propan-1,3-dione;
112. 2-cyano-3-cyclopropyl-1-(2-methylthio-4-pentafluorosulphanylphenyl)propan-1,3-dione;
113. 2-cyano-3-cyclopropyl-1-(2-methylsulphonyl-4-pentafluorosulphanylphenyl)propan- 1, 3- dione;
114. 2-cyano-3-cyclopropyl-1-(2-methylsulphinyl-4-pentafluorosulphanylphenyl)propan-1,3-dione; and 115. 4-cyclopropylcarbonyl-5-(2-methylsulphonyl-4-pentafluorosulphanylphenyl)isoxazole The following compounds of formula (Ia) in which the $SF_5$ group is attached to the 4-position of the phenyl ring form part of the present invention.

In the table that follows "Me" means methyl, "Et" means ethyl, "c-Pr" means cyclopropyl, "Ph" means phenyl. Where subscripts do not appear in the Table it is understood that in appropriate cases they are present. For example, "$CF_3$" is understood to mean —$CF_3$; "NO2" is understood to mean —$NO_2$, etc.

| Cpd.No. | R | R1 | (R2)n |
|---|---|---|---|
| 4 | H | c-Pr | 2-NO2 |
| 5 | H | c-Pr | 2-SMe |
| 6 | H | c-Pr | 2-SOMe |
| 7 | H | c-Pr | 2-SO2Me |
| 8 | H | 1-Me-c-Pr | 2-SMe |
| 9 | H | 1-Me-c-Pr | 2-SOMe |
| 10 | H | 1-Me-c-Pr | 2-SO2Me |
| 11 | CO2Et | c-Pr | 2-SMe |
| 12 | CO2Et | c-Pr | 2-SOMe |
| 13 | CO2Et | c-Pr | 2-SO2Me |
| 14 | H | c-Pr | 2-CH2SMe |
| 15 | H | c-Pr | 2-CH2SOMe |
| 16 | H | c-Pr | 2-CH2SO2Me |
| 17 | H | c-Pr | 2-Cl |
| 18 | CO2Et | c-Pr | 2-Cl |
| 19 | H | 1-Me-c-Pr | 2-Cl |
| 20 | H | c-Pr | 2-SMe-3-Cl |
| 21 | H | c-Pr | 2-SOMe-3-Cl |
| 22 | H | c-Pr | 2-SO2Me-3-Cl |
| 23 | H | c-Pr | 2-SEt |
| 24 | H | c-Pr | 2-SOEt |
| 25 | H | c-Pr | 2-SO2Et |
| 26 | H | c-Pr | 2-SMe-3-Br |
| 27 | H | c-Pr | 2-SMe-3-F |
| 28 | H | c-Pr | 2-F-3-SMe |
| 29 | H | c-Pr | 2-SMe-3-OMe |
| 30 | H | c-Pr | 2-SOMe-3-OMe |
| 31 | H | c-Pr | 2-SO2Me-3-OMe |
| 32 | H | c-Pr | 2-SMe-3-SMe |
| 33 | H | c-Pr | 2-F |
| 34 | H | c-Pr | 2-Me |
| 35 | H | c-Pr | 2-Et |
| 36 | H | c-Pr | 2-OMe |
| 37 | H | c-Pr | 2-Me-3-Cl |
| 38 | H | c-Pr | 2-Me-3-F |
| 39 | H | c-Pr | 2-Me-3-SMe |
| 40 | H | c-Pr | 2-Me-3-SOMe |
| 41 | H | c-Pr | 2-Me-3-SO2Me |
| 42 | H | c-Pr | 2-OMe-3-SMe |
| 43 | H | c-Pr | 2-OMe-3-SOMe |
| 44 | H | c-Pr | 2-OMe-3-SO2Me |
| 45 | H | c-Pr | 2-CH2S(2-SMe-Ph) |
| 46 | H | c-Pr | 2-CH2S(2-SOMe-Ph) |
| 47 | H | c-Pr | 2-CH2S(2-SO2Me-Ph) |
| 48 | H | c-Pr | 2-CH2SPh |
| 49 | H | c-Pr | 2-CH2SOPh |
| 50 | H | c-Pr | 2-CH2SO2Ph |
| 51 | H | c-Pr | 2-Cl-3-OCH2CH2OMe |
| 52 | H | c-Pr | 2-Cl-3-CONMe2 |
| 53 | H | c-Pr | 2-Cl-3-CO2Me |
| 54 | H | c-Pr | 2-NMeSO2Me |
| 55 | H | c-Pr | 2-OSO2Me |
| 56 | H | c-Pr | 2-NMeCO2Me |
| 57 | H | c-Pr | 2-CH2NMeSO2Me |
| 58 | H | c-Pr | 2-CH2NMeCO2Me |
| 59 | H | c-Pr | 2-CH2S-iBu |
| 60 | H | c-Pr | 2-CH2SO-iBu |
| 61 | H | c-Pr | 2-CH2SO2-iBu |

The following compounds of formula (Ia) in which the —$SF_5$ group is attached to the 2-position of the phenyl ring also form part of the present invention.

| Cpd. No. | R | R1 | (R2)n |
|---|---|---|---|
| 62 | H | c-Pr | 4-NO2 |
| 63 | H | c-Pr | 4-Cl |
| 64 | H | c-Pr | 4-Br |
| 65 | H | c-Pr | 4-SMe |
| 66 | H | c-Pr | 4-SOMe |
| 67 | H | c-Pr | 4-SO2Me |
| 68 | H | 1-Me-c-Pr | 4-SMe |
| 69 | CO2Et | c-Pr | 4-SMe |
| 70 | CO2Et | c-Pr | 4-SOMe |
| 71 | CO2Et | c-Pr | 4-SO2Me |
| 72 | H | 1-Me-c-Pr | 4-SOMe |
| 73 | H | 1-Me-c-Pr | 4-SO2Me |
| 74 | H | c-Pr | 3-F-4SMe |
| 75 | H | c-Pr | 3-F-4-SOMe |
| 76 | H | c-Pr | 3-F-4-SO2Me |
| 77 | H | c-Pr | 3-OMe-4-SMe |
| 78 | H | c-Pr | 3-OMe-4-SOMe |
| 79 | H | c-Pr | 3-OMe-4-SO2Me |
| 80 | H | c-Pr | 3-SMe-4-SMe |
| 81 | H | c-Pr | 3-SMe-4-Cl |
| 82 | H | c-Pr | 3-SOMe-4-Cl |
| 83 | H | c-Pr | 3-SO2Me-4-Cl |
| 84 | H | c-Pr | 3-Cl-4-SMe |
| 85 | H | c-Pr | 3-Cl-4-SOMe |
| 86 | H | c-Pr | 3-Cl-4-SO2Me |
| 87 | H | c-Pr | 3-Me-4-SMe |
| 88 | H | c-Pr | 3-Me-4-SOMe |
| 89 | H | c-Pr | 3-Me-4-SO2Me |
| 90 | H | c-Pr | 3-SMe-4-Me |
| 91 | H | c-Pr | 3-SOMe-4-Me |
| 92 | H | c-Pr | 3-SO2Me-4-Me |
| 93 | H | c-Pr | 3-SMe-4-OMe |
| 94 | H | c-Pr | 3-SOMe-4-OMe |
| 95 | H | c-Pr | 3-SO2Me-4-OMe |
| 96 | H | c-Pr | 3-SMe |
| 97 | H | c-Pr | 3-SOMe |
| 98 | H | c-Pr | 3-SO2Me |
| 99 | H | c-Pr | 4-CH2SMe |
| 100 | H | c-Pr | 4-CH2SOMe |
| 101 | H | c-Pr | 4-CH2SO2Me |
| 102 | CO2Et | c-Pr | 3-F-4-SMe |
| 103 | CO2Et | c-Pr | 3-OMe-4-SMe |
| 104 | CO2Et | c-Pr | 3-SMe-4-SMe |
| 105 | CO2Et | c-Pr | 3-SMe-4-Cl |
| 106 | CO2Et | c-Pr | 3-Cl-4-SOMe |
| 107 | CO2Et | c-Pr | 3-Me-4-SOMe |
| 108 | CO2Et | c-Pr | 3-SO2Me-4-Me |
| 109 | CO2Et | c-Pr | 3-SO2Me |

Compounds of formula (I) may be prepared by the application or adaptation of known methods (i.e. methods heretofore used or described in the literature), for example as hereinafter described.

In the following description where symbols appearing in formulae are not specifically defined, it is to be understood that they are "as hereinbefore defined" in accordance with the first definition of each symbol in the specification.

It is to be understood that in the descriptions of the following processes the sequences may be performed in different orders, and that suitable protecting groups may be required to achieve the compounds sought.

It is understood that when a process of the invention leads to the formation of a mixture of (Ia) and (Ib), these compounds may be separated by known methods.

According to a feature of the present invention compounds of formula (Ia) or (Ib) in which R represents hydrogen and $R^1$, $R^2$ and n are as defined above may be prepared by the reaction of a compound of formula (II):

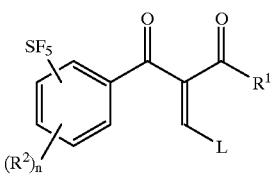

(II)

wherein L is a leaving group and $R^1$, $R^2$ and n are as hereinbefore defined, with hydroxylamine or a salt of hydroxylamine. Hydroxylamine hydrochloride is generally preferred. Generally L is alkoxy, for example ethoxy, or N,N-dialkylamino, for example dimethylamino. The reaction is generally carried out in an organic solvent such as ethanol or acetonitrile or a mixture of a water-miscible organic solvent and water, preferably in a ratio of organic solvent: water of from 1:99 to 99:1, optionally in the presence of a base or acid acceptor such as triethylamine or sodium acetate at a temperature from room temperature to the boiling point of the solvent.

Intermediates of formula (II) are novel and as such form a further feature of the invention.

According to a further feature of the present invention compounds of formula (Ia) in which R represents hydrogen and $R^1$, $R^2$ and n are as defined above may be prepared by the reaction of a compound of formula (III):

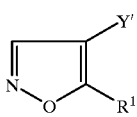

(III)

wherein $R^1$ is as hereinbefore defined and Y' represents a carboxy group or a reactive derivative thereof (such as a carboxylic acid chloride or carboxylic ester), or a cyano group, with an appropriate organometallic reagent such as a Grignard reagent or an organolithium reagent. The reaction is generally carried out in an inert solvent such as ether or tetrahydrofuran at a temperature from 0° C. to the reflux temperature of the mixture.

According to a further feature of the present invention compounds of formula (Ia) wherein R represents a group —$CO_2R^3$ and $R^1$, $R^2$ and n are as defined above, may be prepared by the reaction of a compound of formula (IV):

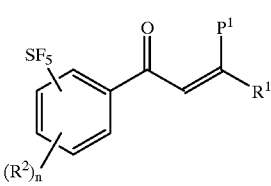

(IV)

wherein $R^1$, $R^2$ and n are as hereinbefore defined and $p^1$ is a leaving group such as N,N-dialkylamino, with a compound of formula $R^3O_2CC(Z^1)$=NOH wherein $R^3$ is as hereinbefore defined and $Z^1$ is a halogen atom. Generally $Z^1$ is chlorine or bromine. The reaction is generally performed in an inert solvent such as toluene or dichloromethane either in the presence of a base such as triethylamine or a catalyst such as a 4 Angstrom molecular sieve or fluoride ion. Intermediates of formula (IV) are novel and as such form a further feature of the invention.

According to a further feature of the present invention compounds of formula (Ia) in which R represents a group —$CO_2R^3$ and $R^1$, $R^2$ and n are as defined above may be prepared by the reaction of a compound of formula (V):

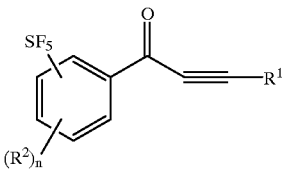

(V)

wherein $R^1$, $R^2$ and n are as hereinbefore defined, with a compound of formula $R^3O_2CC(Z^1)$=NOH wherein $Z^1$ and $R^3$ are as hereinbefore defined. The reaction is generally performed in an inert solvent such as toluene or dichloromethane optionally in the presence of a base such as triethylamine or a catalyst such as a 4 Angstrom molecular sieve or fluoride ion. The reaction is preferably carried out at a temperature between room temperature and the reflux temperature of the mixture. Intermediates of formula (V) are novel and as such form a further feature of the invention.

According to a further feature of the present invention compounds of formula (Ia) or (Ib) wherein R represents —$CO_2R^3$ and $R^1$, $R^2$ and n are as defined above, may be prepared by the reaction of a salt of compounds of formula (VI):

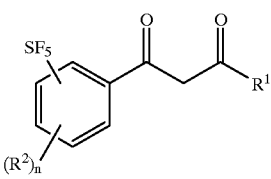

(VI)

wherein $R^1$, $R^2$ and n are as hereinbefore defined with a compound of formula $R^3O_2CC(Z^1)$=NOH wherein $R^3$ and $Z^1$ are as hereinbefore defined. Preferred salts include sodium or magnesium salts. The reaction is generally performed in an inert solvent such as dichloromethane or acetonitrile at a temperature between room temperature and the reflux temperature of the mixture. The salt of a compound of formula (VI) is generally prepared in situ by treating the compound of formula (VI) with a base. Examples of suitable bases include alkaline earth metal alkoxides such as magnesium methoxide. Intermediates of formula (VI) are novel and as such form a further feature of the invention.

According to a feature of the present invention compounds of formula (Ib) in which R, $R^1$, $R^2$ and n are as defined above, may be prepared by the metallation of a compound of general formula (VII):

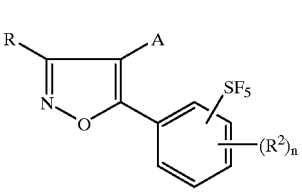

(VII)

wherein R, $R^2$ and n are as defined above and A is a halogen atom, followed by reaction of the compound thus obtained with an acid chloride of formula $R^1COCl$ wherein $R^1$ is as defined above. Generally A is bromine or iodine and the reaction performed with for example n-butyllithium in an inert solvent such as ether or tetrahydrofuran at a temperature from −78° C. to 0° C. Compounds of formula (VII) are novel and as such constitute a further feature of the invention.

According to a further feature of the present invention compounds of formula (Ib) in which R, $R^1$, $R^2$ and n are as defined above may be prepared by the oxidation of a compound of formula (VIII):

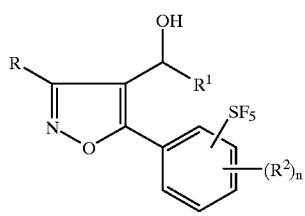
(VIII)

wherein R, $R^1$, $R^2$ and n are as defined above, to convert the hydroxy group to a ketone group. The reaction is generally performed using an appropriate oxidising agent, for example, a mixture prepared from chromium trioxide and aqueous sulphuric acid. Compounds of formula (VIII) are novel and as such constitute a further feature of the invention.

According to a further feature of the present invention compounds of formula (Ib) in which R represents hydrogen and $R^1$, $R^2$ and n are as defined above may be prepared by the reaction of a compound of formula (IX):

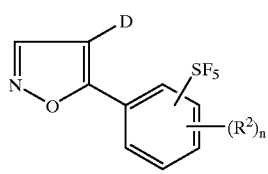
(IX)

in which $R^2$ and n are as defined above and D represents a carboxy group, or a reactive derivative thereof (such as a carboxylic acid chloride or carboxylic ester), or a cyano group, with an appropriate organometallic reagent such as a Grignard reagent or an organolithium reagent. The reaction is generally carried out in an inert solvent such as ether or tetrahydrofuran, at a temperature from 0° C. to the reflux temperature of the solvent. Intermediates of formula (IX) are novel and as such form a further feature of the invention.

According to a further feature of the present invention compounds of formula (Ib) in which R represents a $—CO_2R^3$ group and $R^1$, $R^2$ and n are as defined above, may be prepared by the reaction of a compound of general formula (X):

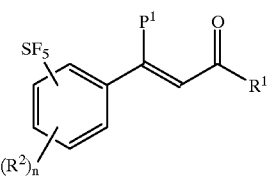
(X)

wherein $R^1$, $R^2$ and n are as defined and $p^1$ is as defined above, with a compound of formula $R^3O_2CC(Z^1)=NOH$ wherein $Z^1$ and $R^3$ are as hereinbefore defined. Generally $Z^1$ is chlorine or bromine. The reaction is preferably performed in an inert solvent such as toluene or dichloromethane either in the presence of a base such as triethylamine or a catalyst such as a 4 Angstrom molecular sieve or fluoride ion. Intermediates of formula (X) are novel and as such form a further feature of the invention.

According to a further feature of the present invention compounds of formula (Ib) in which R represents a group $—CO_2R^3$ and $R^1$, $R^2$ and n are as defined above may be prepared by the reaction of a compound of formula (XI):

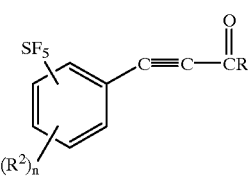
(XI)

wherein $R^1$, $R^2$ and n are as defined above, with a compound of formula $R^3O_2CC(Z^1)=NOH$ wherein $Z^1$ and $R^3$ are as hereinbefore defined. Generally $Z^1$ is chlorine or bromine. The reaction is preferably performed in an inert solvent such as toluene or dichloromethane, either in the presence of a base such as triethylamine, or a catalyst such as a 4 Angstrom molecular sieve or fluoride ion. Intermediates of formula (XI) are novel and as such form a further feature of the invention.

According to a feature of the present invention compounds of formula (Ic) may be prepared from the corresponding compound of formula (Ia) or (Ib) in which R is as defined above, or in which R is replaced by an amide or nitrile. Where R represents a hydrogen atom the reaction is preferably carried out by treatment with a base. Examples of suitable bases include alkali or alkaline earth metal hydroxides, alkoxides such as sodium ethoxide or organic bases such as triethylamine. Where R represents $—CO_2R^3$, or where R is replaced by amide or nitrile, the conversion is generally carried out by a hydrolytic reaction. The hydrolytic reaction may be performed in the presence of an acid or base. Acidic hydrolysis may be achieved for example using aqueous hydrochloric acid. Basic hydrolysis may be achieved for example using sodium hydroxide in a mixture of alcohol and water. The reactions are preferably carried out at a temperature between room temperature and the reflux temperature of the mixture. Compounds of formula (Ia) or (Ib) in which R is replaced by amide or nitrile are novel and thus constitute a further feature of the invention.

According to a further feature of the present invention, compounds of formula (Ic) in which $R^1$, $R^2$ and n are as defined above may also be prepared by the reaction of a benzoyl chloride of formula (XII):

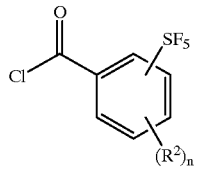
(XII)

wherein $R^2$ and n are as hereinbefore defined, with a beta-ketonitrile of formula (XIII):

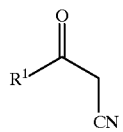
(XIII)

wherein $R^1$ is as hereinbefore defined. The reaction is generally performed in the presence of a base, in a solvent or solvent mixture. Suitable bases include metal hydrides, hydroxides or alkoxides (e.g. sodium or lithium hydride, sodium hydroxide, potassium hydroxide, magnesium ethoxide or magnesium methoxide). Suitable solvents include for example tetrahydrofuran; hydrocarbons such as toluene; or halogenated hydrocarbons such as dichloromethane. The reaction is generally performed at a temperature from 0° C. to the reflux temperature. A number of compounds of formula (XII) are novel and thus form a further feature of the invention.

According to a further feature of the present invention, compounds of formula (Ic) in which $R^1$, $R^2$ and n are as defined above may also be prepared by the reaction of an acid chloride of formula $R^1COCl$ wherein $R^1$ is as hereinbefore defined, with a beta-ketonitrile of formula (XIV):

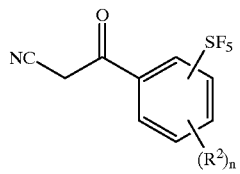
(XIV)

wherein $R^2$ and n are as hereinbefore defined. The reaction is generally performed under the same conditions as described above for the reaction of compounds of formula (XII) with compounds of formula (XIII). Intermediates of formula (XIV) are novel and as such form a further feature of the invention.

According to a further feature of the present invention compounds of formula (Ic) in which $R^1$, $R^2$ and n are as defined above may also be prepared by the reaction of a benzoyl chloride of formula (XII) above wherein $R^2$ and n are as hereinbefore defined, with a beta-ketonitrile of formula (XIII) wherein $R^1$ is as hereinbefore defined, via an intermediate of formula (XV):

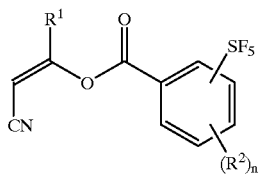
(XV)

wherein $R^1$, $R^2$ and n are as hereinbefore defined. The formation of the intermediate of formula (XV) may be carried out in the presence of a mild base such as an organic base e.g. triethylamine, in an inert solvent such as acetonitrile or dichloromethane at a temperature between room temperature and the reflux temperature of the mixture. The rearrangement of the intermediate of formula (XV) to a compound of formula (Ic) is generally carried out in situ in an inert solvent such as acetonitrile or dichloromethane in the presence of a catalyst such as a source of cyanide. Examples of such sources of cyanide are acetone cyanohydrin or an alkali metal cyanide such as potassium cyanide, optionally in the presence of a crown ether such as 18-crown-6. Intermediates of formula (XV) are novel and as such constitute a further feature of the invention.

According to a further feature of the present invention compounds of formula (Ic) in which $R^1$, $R^2$ and n are as defined above, may be prepared by the reaction of an acid chloride of formula $R^1COCl$ wherein $R^1$ is as hereinbefore defined, with a beta-ketonitrile of formula (XIV) wherein $R^2$ and n are as hereinbefore defined via an intermediate of formula (XVI):

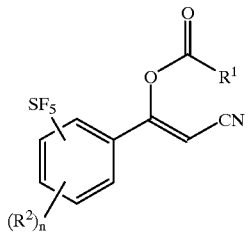
(XVI)

wherein $R^1$, $R^2$ and n are as hereinbefore defined. The formation and rearrangement of the intermediate of formula (XVI) is generally carried out under the same conditions as described above for the formation and rearrangement of compounds of formula (XV). Intermediates of formula (XVI) are novel and as such form a further feature of the invention.

Intermediates in the preparation of compounds of formula (Ia), (Ib) and (Ic) may be prepared by the application or adaptation of known methods.

Intermediates of formula (Ia) or (Ib) in which R is replaced by an amide or nitrile may be prepared by the reaction of a salt of a compound of formula (VI) with a compound of formula $P^2C(Z^1)=NOH$ in which $p^2$ is amide or nitrile. The reaction is performed using the same conditions as described for the preparation of compounds of formula (Ia) or (Ib) in which R is $—CO_2R^3$ from compounds of formula (VI).

Compounds of formula (II) may be prepared by the reaction of compounds of formula (VI) with either a trialkyl orthoformate such as triethyl orthoformate or a dimethylformamide dialkyl acetal such as dimethylformamide dimethyl acetal. The reaction with a trialkyl orthoformate can be carried out in the presence of acetic anhydride at the reflux temperature of the mixture and the reaction with dialkylformamide dialkyl acetal is carried out optionally in the presence of an inert solvent at a temperature from room temperature to the reflux temperature of the mixture.

Compounds of formula (IV) may be prepared by the reaction of a compound of formula (XVII) with a benzoyl chloride of formula (XII):

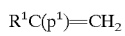
(XVII)

wherein $R^1$ and $p^1$ are as defined above.

The reaction is generally carried out in the presence of an organic base such as triethylamine in an inert solvent such as toluene or dichloromethane at a temperature between −20° C. and room temperature.

Compounds of formula (V) may be prepared by the metallation of the appropriate acetylene of formula (XVIII):

(XVIII)

followed by reaction of the metal salt thus obtained with a benzoyl chloride of formula (XII). The metallation is generally performed using n-butyl lithium in an inert solvent such as ether or tetrahydrofuran at a temperature from −78° C. to 0° C. The subsequent reaction with the benzoyl chloride is carried out in the same solvent at a temperature between −78° C. and room temperature.

Compounds of formula (VI) may be prepared by the reaction of an acid chloride of formula (XII) with the metal salt of a compound of formula (XIX):

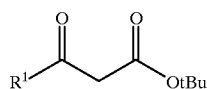
(XIX)

wherein $R^1$ is as hereinbefore defined, to give a compound of formula (XX):

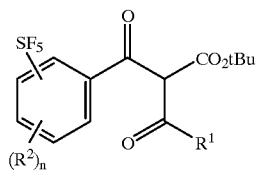
(XX)

wherein $R^1$, $R^2$ and n are as hereinbefore defined, which is subsequently decarboxylated to give a compound of formula (VI). Generally the reaction to produce the compound of formula (XX) is performed in a solvent such as a lower alcohol, preferably methanol, in the presence of a metal, preferably magnesium. The reaction may also be performed using a pre-prepared metal salt of a compound of formula (XIX). The decarboxylation is generally performed by refluxing the compound of formula (XX) in the presence of a catalyst, such as para-toluenesulphonic acid or trifluoroacetic acid, in an inert solvent e.g. toluene or 1,2-dichloroethane.

Compounds of formula (VI) may also be prepared by the reaction of a benzoic acid ester of formula (XXI):

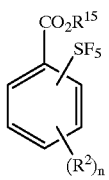
(XXI)

wherein $R^2$ and n are as hereinbefore defined and $R^{15}$ represents straight- or branched- chain $C_{1-6}$ alkyl, with a compound of formula (XXII):

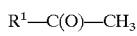
(XXII)

wherein $R^1$ is as hereinbefore defined. The reaction is generally performed in a solvent such as ether, tetrahydrofuran or N,N-dimethylformamide, in the presence of a base, preferably an alkali metal base such as sodium hydride, at a temperature from 0° C. to the reflux temperature.

Acid chlorides of formula (XII) may be prepared by the reaction of a benzoic acid of formula (XXIII):

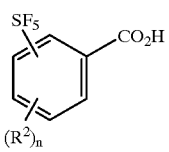
(XXIII)

with a chlorinating agent, for example thionyl chloride at the reflux temperature of the mixture. In some cases the benzoyl chlorides may also be prepared by reaction of the benzoic acid with oxalyl chloride in a solvent such as 1,2-dichloroethane at from ambient to reflux temperature.

Benzoic acids of formula (XXIII) are novel with the exclusion of those in which n is zero and the —$SF_5$ group is located m- or p- to the carboxy group (these compounds being reported by W. A. Sheppard in J.Am.Chem.Soc. 1962, 84, 3064–3072) and as such constitute a further feature of the present invention.

Esters of formula (XXI) are novel and as such constitute a further feature of the present invention.

Esters of formula (XXI) may be prepared from acids of formula (XXIII) by known methods.

Compounds of general formula (VIII) may be prepared by metallation of compounds of general formula (VII) wherein A represents bromine or iodine with for example n-butyllithium in an inert solvent such as ether or tetrahydrofuran at a temperature from −78° C. to 0° C., followed by reaction with an aldehyde of general formula $R^1$CHO.

Compounds of general formula (IX) wherein D is —$CO_2$-alkyl or —CN may be prepared by the reaction of compounds of general formula (XXIV):

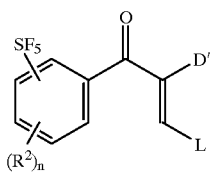

(XXIV)

wherein D' represents $CO_2$-alkyl or —CN and L is as hereinbefore defined, with a salt of hydroxylamine such as hydroxylamine hydrochloride, in a solvent such as ethanol or acetonitrile, optionally in the presence of a base or acid acceptor such as triethylamine or sodium acetate.

Compounds of general formula (IX) in which D represents a carboxylic acid or carboxylic acid chloride may be prepared from the corresponding compound of general formula (IX) in which D represents a carboxylic ester group by the hydrolysis of said ester group and conversion, as necessary, of the acid thus obtained to the acid chloride, e.g. by heating with thionyl chloride.

Compounds of general formula (XXIV) may be prepared by the reaction of a ketoester or ketonitrile of general formula (XXV):

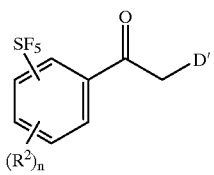

(XXV)

with either triethyl orthoformate in the presence of acetic anhydride at the reflux temperature of the mixture or with dimethylformamide dimethylacetal optionally in an inert solvent such as toluene at a temperature from room temperature to the reflux temperature of the mixture.

Compounds of general formula (X) may be prepared by the reaction of a compound of general formula (XXVI):

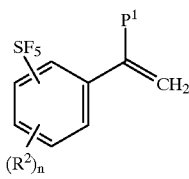

(XXVI)

wherein $p^1$ is as hereinbefore defined, with an acid chloride of general formula $R^1COCl$ in an inert solvent such as dichloromethane or toluene, in the presence of a base such as triethylamine.

Compounds of general formula (XI) may be prepared by the metallation of the appropriate phenylacetylene of general formula (XXVII):

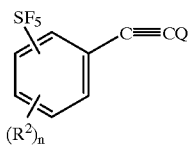

(XXVII)

wherein Q represents hydrogen or a bromine or iodine atom, using for example n-butyllithium in an inert solvent such as ether or tetrahydrofuran at a temperature from −78° C. to 0° C., followed by treatment with an acid chloride of general formula $R^1COCl$.

Compounds of general formula (VII) may be prepared by the halogenation of compounds of general formula (XXVIII):

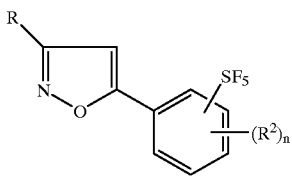

(XXVIII)

for example by heating with bromine or iodine in the presence of concentrated nitric acid.

Compounds of general formula (XXVIII) may be prepared by the reaction of compounds of general formula (XXIX):

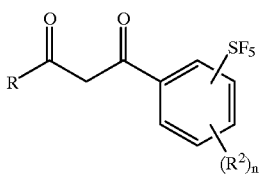

(XXIX)

with a salt of hydroxylamine such as hydrochloride, in a solvent such as ethanol or acetonitrile, optionally in the presence of a base or acid acceptor such as triethylamine or sodium acetate.

Beta-ketonitriles of formula (XIII) may be prepared from acid chlorides of formula $R^1COCl$ by a number of methods well known in the chemical literature. For example, see Krauss, et al, Synthesis, 1983, 308, or Muth, et al, J. Org. Chem, 1960, 25, 736. Alternatively beta-ketonitriles of formula (XIII) may be prepared by the reaction of an ester of formula $R^1$—$CO_2Et$, wherein $R^1$ is as hereinbefore defined, with acetonitrile. This reaction is described in the literature, for example see the article by Abramovitch and Hauser, J. Am. Chem. Soc., 1942, 64, 2720.

Beta-ketonitriles of formula (XIV) may be prepared from benzoyl chlorides of formula (XII) or from corresponding ethyl benzoates in a manner analogous to the preparation of beta-ketonitriles of formula (XIII) set forth above.

According to a further feature of the invention benzoic acids of formula (XXIII) may be prepared by the reaction of a compound of formula (XXX):

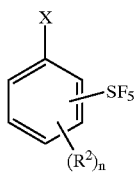

(XXX)

wherein X represents an iodine, chlorine or preferably bromine atom and $R^2$ is as defined above, with an organometallic reagent, generally a Grignard or organolithium reagent. Preferably n-butyl lithium is employed (in which case X is an iodine or bromine atom) in an inert solvent, for example ether at a temperature from −78° C. to 20° C., followed by reaction with carbon dioxide or a source thereof.

The intermediate halides of formula (XXX) may be prepared according to known methods, for example as described in J.Am.Chem.Soc. 84, 3064 (1962).

Intermediates of formula (III), (XVII), (XVIII), (XIX) and (XXII) are known or may be prepared by the application or adaptation of known methods.

Those skilled in the art will appreciate that some compounds of formula (I) may be prepared by the interconversion of other compounds of formula (I) and such interconversions constitute yet more features of the present invention.

According to a further feature of the present invention compounds in which p or q is one or two may be prepared by the oxidation of the sulphur atom of the corresponding compounds in which p or q is zero or one. The oxidation of the sulphur atom is generally carried out using for example 3-chloroperoxybenzoic acid in an inert solvent such as dichloromethane at a temperature from −40° C. to room temperature.

Agriculturally acceptable salts or metal complexes of compounds of formulae (Ia), (Ib) or (Ic) can be prepared using known methods, or by the application of known methods.

The following non-limiting Examples illustrate the preparation of compounds of formula (I) and the Reference Examples illustrate the preparation of intermediates in their synthesis. NMR Spectra are recorded as δ (ppm) in deuterochloroform as solvent.

EXAMPLE 1

Hydroxylamine hydrochloride (0.42 g) was added to a stirred solution of 3-cyclopropyl-2-ethoxymethylene-1-(4-pentafluorosulphanyl-phenyl)-propan-1,3-dione (0.97 g) in ethanol. Anhydrous sodium acetate (0.49 g) was then added and stirring maintained for 1 hour. The solvent was evaporated and the residue distributed between dichloromethane and water. The organic phase was dried (magnesium sulphate) and evaporated, and the residual oil purified by chromatography eluting with ethyl acetate/hexane to give after trituration with hexane 5-cyclopropyl-4-(4-pentafluorosulphanyl-benzoyl)isoxazole (Compound 1) as a white solid, m.p.57–58° C. Further elution gave, after trituration with hexane, 4-cyclopropylcarbonyl-5-(4-pentafluorosulphanylphenyl)isoxazole (Compound 2) as a white solid, m.p.53–55° C.

The following compounds were prepared in a similar manner:

5-cyclopropyl-4-(2-methylthio-4-pentafluorosulphanylbenzoyl)isoxazole (Compound 5), m.p.80–81° C. and 4-cyclopropylcarbonyl-5-(2-methylthio-4-pentafluorosulphanylphenyl)isoxazole (Compound 110), NMR 0.98 (m,2H), 1.21 (m,2H), 2.0 (m,1H), 2.5 (s,3H), 7.58 (d,1H), 7.68–7.73 (m,2H), 8.8 (s,1H); and 5-cyclopropyl-4-(2-nitro-4-pentafluorosulphanylbenzoyl)isoxazole (Compound 4),m.p. 132–133° C.

EXAMPLE 2

Triethylamine (0.73 g) was added to a stirred solution of 4-cyclopropylcarbonyl-S-(4-pentafluorosulphanylphenyl)isoxazole (Compound 2, 0.4 g) in dichloromethane. After 16 hours the solution was washed (2M hydrochloric acid), dried (magnesium sulphate) and evaporated to dryness. The residue was purified by chromatography eluting with ethyl acetate/hexane to give a residue which was suspended in dichloromethane and shaken with hydrochloric acid until dissolved. The organic phase was evaporated and triturated with hexane to give 2-cyano-3-cyclopropyl-1-(4-pentafluorosulphanylphenyl)propan-1,3-dione as a white solid (Compound 3, m.p.108–110° C.

The following compounds were prepared in a similar manner:

2-cyano-3-cyclopropyl-1-(2-nitro-4-pentafluorosulphanylphenyl)propan-1,3-dione (Compound 111), m.p.120–121° C.;

2-cyano-3-cyclopropyl-1-(2-methylthio-4-pentafluorosulphanylphenyl)propan-1,3-dione (Compound 112), m.p.93° C.;

2-cyano-3-cyclopropyl-1-(2-methylsulphonyl-4-pentafluorosulphanylphenyl)propan-1,3-dione (Compound 113), m.p.189–190° C.; and 2-cyano-3-cyclopropyl-1-(2-methylsulphinyl-4-pentafluorosulphanylphenyl)propan-1,3-dione (Compound 114), m.p.146–148° C.

EXAMPLE 3

3-Chloroperbenzoic acid (0.95 g of 70%) was added to a solution of 5-cyclopropyl-4-(2-methylthio-4-pentafluorosulphanyl-benzoyl)isoxazole (0.6 g) in dichloromethane and stirred overnight at 20° C., cooled, filtered and the filtrate washed in turn with sodium metabisulphite solution, sodium acetate solution and water. The organic phase was dried (magnesium sulphate), evaporated and the residue washed (hexane) to give 5-cyclopropyl-4-(2-methylsulphonyl-4-pentafluorosulphanylbenzoyl)isoxazole (0.37 g, Compound 7), m.p.168–170° C.

By proceeding in a similar manner but employing the appropriate amount of 3-chloroperbenzoic acid there was obtained:

5-cyclopropyl-4-(2-methylsulphinyl-4-pentafluorosulphanylbenzoyl)isoxazole (0.37 g, Compound 6), m.p.174–175° C.

EXAMPLE 4

By proceeding according to the method of Example 3 there was prepared from 4-cyclopropylcarbonyl-5-(2-methylthio-4-pentafluorosulphanylphenyl)isoxazole the following compound:

4-cyclopropylcarbonyl-5-(2-methylsulphonyl-4-pentafluorosulphanylphenyl)isoxazole (Compound 115), m.p.143–145° C.

Reference Example 1

A mixture of 3-cyclopropyl-1-(4-pentafluorosulphanylphenyl)-propan-1,3-dione (0.82 g) and triethylorthoformate (3.1 g) in acetic anhydride (40 ml) was heated at reflux temperature for 6 hours. The excess reagent and solvent were evaporated to give 3-cyclopropyl-2-ethoxymethylene-1-(4-pentafluorosulphanylphenyl)-propan-1,3-dione (1.0 g) as an orange oil. This was used directly in the subsequent reaction stage.

By proceeding in a similar manner the following compounds were prepared:

3-cyclopropyl-2-ethoxymethylene-1-(2-methylthio-4-pentafluorosulphanylphenyl)propan-1,3-dione; and 3-cyclopropyl-2-ethoxymethylene-1-(2-nitro-4-pentafluorosulphanylphenyl)propan-1,3-dione.

Reference Example 2

A solution of t-butyl 3-cyclopropyl-3-oxopropionate magnesium enolate (1.43 g, prepared from t-butyl 3-cyclopropyl-3-oxopropionate and magnesium turnings in methanol) in toluene was stirred at room temperature. A solution of 4-pentafluorosulphanylbenzoyl chloride (1.07 g) in toluene was added. After 2 hours, hydrochloric acid (2M) was added and the mixture vigorously stirred for 15 minutes. The organic phase was dried by azeotropic removal of solvent. 4-Toluenesulphonic acid (0.1 g) was added and the solution heated at reflux for 3.5 hours. The cooled solution was washed (water), dried (magnesium sulphate) and evaporated. Purification of the residue by chromatography, eluting with ethyl acetate/hexane gave 3-cyclopropyl-1-(4-pentafluorosulphanylphenyl)propan-1,3-dione as a fawn solid (1.0 g), m.p.70–72° C.

By proceeding in a similar manner the following compounds were prepared:

3-cyclopropyl-1-(2-methylthio-4-pentafluorosulphanylphenyl)propan-1,3-dione, NMR 1.02 (m,2H), 1.25 (m,2H), 1.8 (m,1H), 2.52 (s,3H), 6.11 (s,2H), 7.55–7.65 (m,3H); and 3-cyclopropyl-1-(2-nitro-4-pentafluorosulphanylphenyl) propan-1,3-dione, m.p.108–110° C.

Reference Example 3

Oxalyl chloride (1.53 g) was added to a stirred solution of 4-pentafluorosulphanyl-benzoic acid (0.99 g) in dichloroethane. A solution of N,N-dimethylformamide in dichloromethane (3 ml of a solution prepared by the addition of 2 drops of N,N-dimethylformamide to 10 ml of dichloromethane) was added. After 15 minutes the solution was heated for a further 15 minutes at 45° C., and evaporated to dryness to give 4-pentafluorosulphanylbenzoyl chloride as an orange oil (1.07 g). This was used directly in the subsequent reaction stage.

By proceeding in a similar manner the following compounds were prepared:

2-methylthio-4-pentafluorosulphanylbenzoyl chloride; and 2-nitro-4-pentafluorosulphanylbenzoyl chloride.

Reference Example 4

A solution of n-butyllithium (9.4 ml of a 1.6M solution in hexane) was added to a stirred solution of 4-bromophenylsulphur pentafluoride (3.87 g) in ether at −78° C. under an inert atmosphere. After maintaining at −78° C. for 1 hour, solid carbon dioxide (20 g) was added and the mixture allowed to warm to 5° C. during 1.5 hours. Hydrochloric acid (2M) was added, the mixture stirred for 0.5 hour and the organic phase separated and itself extracted with sodium carbonate solution. The basic extract was washed (ether) and acidified (hydrochloric acid). The precipitated solid was extracted (ether), dried (magnesium sulphate) and evaporated. The residue was triturated (hexane) to give 4-pentafluorosulphanylbenzoic acid as a fawn solid (1.2 g), m.p.188–190° C.

Reference Example 5

A solution of 4-aminophenylsulphur pentafluoride (4.38 g) in acetonitrile was added dropwise at −2° C. to 1° C. during 15 minutes to a stirred mixture of copper (II) bromide (4.46 g) and t-butyl nitrite (5.15 g) in acetonitrile. Stirring was continued at 0° C. for 15 minutes and then at ambient temperature for 4 hours. The mixture was poured into water, acidified to pH 1 with 2M hydrochloric acid, and extracted (ether). The extract was washed (water), dried (magnesium sulphate) and evaporated to dryness to give 4-bromophenylsulphur pentafluoride as a dark oil (5.9 g), NMR (CDCl$_3$) 7.66 (s,4H).

By proceeding in a similar manner 4-bromo-3-nitrophenylsulphur pentafluoride as an orange oil was prepared, single peak by gas chromatography (Megabore OV1 type column).

Reference Example 6

A mixture of 2-methylthio-4-pentafluorosulphanylbenzonitrile (0.47 g) and sodium hydroxide (0.2 g) in a mixture of water and ethylene glycol (1:5) was heated at reflux for 5 hours. The cooled mixture was diluted (water), acidified (hydrochloric acid) and the solid filtered, washed (water) and dried to give 2-methylthio-4-pentafluorosulphanylbenzoic acid (0.38g), m.p.150–152° C.

Reference Example 7

2-Nitro-4-pentafluorosulphanylbenzonitrile (6.6 g) was added to a mixture of water and sulphuric acid (1:1) and the mixture stirred and heated at reflux for 3.5 hours. The cooled mixture was poured onto ice/water, extracted (ether) and the organic phase then extracted into sodium carbonate solution (2N). The basic extract was washed (ether), acidified (hydrochloric acid) and extracted (ether). The ethereal layer was washed (water), dried (magnesium sulphate) and evaporated to give 2-nitro-4-pentafluorosulphanylbenzoic acid. (5.97 g), m.p.165–167° C.

Reference Example 8

Sodium thiomethoxide (8.97 g) was added to a solution of 2-nitro-4-pentafluorosulphanylbenzonitrile (11.7 g) in acetone and stirred at 20° C. overnight, then evaporated and purified by column chromatography on silica gel eluting with ethyl acetate/hexane (3:97) to give 2-methylthio-4-pentafluorosulphanylbenzonitrile (4.65 g), m.p.101–102° C.

Reference Example 9

Copper (I) cyanide (5.05 g) was added to a stirred solution of 4-bromo-3-nitro-phenylsulphur pentafluoride (18.5 g) in N,N-dimethylformamide and heated at 14° C. for 4 hours. A mixture of ferric chloride (20.0 g),concentrated hydrochloric acid and water was added at 105° C. and heating continued for 1.25 hours. The cooled mixture was diluted with water, extracted (ether) and the organic phase washed (water), dried (magnesium sulphate) and evaporated to give 2-nitro-4-pentafluorosulphanylbenzonitrile (14.7 g), m.p.57–59° C.

Reference Example 10

4-Acetamido-3-nitrophenylsulphur pentafluoride (29.0 g) was heated at reflux with hydrochloric acid (6N) and dioxan for 40 minutes and concentrated to low volume, basified with sodium carbonate solution and extracted (ether). The extract was washed (water), dried (magnesium sulphate) and evaporated to give 4-amino-3-nitrophenylsulphur pentafluoride (24.7 g), m.p.132–135° C.

Reference Example 11

4-Acetamidophenylsulphur pentafluoride (27.0 g) was added during 5 minutes to a stirred mixture of concentrated nitric acid and concentrated sulphuric acid (1 part:2 parts by volume) at 0–5° C. After 5 minutes acetic acid (1 part) was added and stirring continued at 5° C. for 1.5 hours. The mixture was added to ice/water, extracted (ethyl acetate) and the extract washed (sodium carbonate solution), dried (magnesium sulphate) and evaporated. The residue was triturated with ether to give 4-acetamido-3-nitrophenylsulphur pentafluoride (30.0 g), m.p.135–138° C.

Reference Example 12

Acetic anhydride was added during 5 minutes to a stirred solution of 4-aminophenylsulphur pentafluoride (30.2 g) in acetic acid at 40° C. and then heated at 65° C. for 0.5 hour. The cooled mixture was added to water, stirred for 1 hour and filtered. The solid was washed with water, sodium bicarbonate solution and water, dried and purified by stirring with hexane to give 4-acetamidophenylsulphur pentafluoride (27.0 g), m.p.131–132° C.

According to a feature of the present invention, there is provided a method for controlling the growth of weeds (i.e. undesired vegetation) at a locus which comprises applying to the locus a herbicidally effective amount of at least one isoxazole or 2-cyano-1,3-dione derivative of formula (I) or an agriculturally acceptable salt or metal complex thereof. For this purpose, the isoxazole or 2-cyano-1,3-dione derivatives are normally used in the form of herbicidal compositions (i.e. in association with compatible diluents or carriers and/or surface active agents suitable for use in herbicidal compositions), for example as hereinafter described.

The compounds of formula (I) show herbicidal activity against dicotyledonous (i.e. broad-leafed) and monocotyledonous (i.e. grass) weeds by pre- and/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil.

For example, the compounds of formula (I) may be used to control the growth of:

broad-leafed weeds, for example, *Abutilon theophrasti, Amaranthus retroflexus, Bidens pilosa, Chenopodium album, Galium aparine, Ipomoea spp.* e.g. *Ipomoea purpurea, Sesbania exaltata, Sinapis arvensis, Solanum nigrum* and *Xanthium strumarium*, and grass weeds, for example *Alopecurus myosuroides, Avena fatua, Digitaria sanquinalis, Echinochloa crus-galli, Sorghum bicolor, Eleusine indica* and *Setaria spp*, e.g. *Setaria faberii* or *Setaria viridis*, and sedges, for example, *Cyperus esculentus*.

The amounts of compounds of formula (I) applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 5 kg of active material per hectare give good results. However, it is to be understood that higher or lower application rates may be used, depending upon the particular problem of weed control encountered.

The compounds of formula (I) may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 0.01 kg and 4.0 kg, and preferably between 0.01 kg and 1.0 kg, more preferably from 0.01 kg to 0.5 kg of active material per hectare are particularly suitable.

The compounds of formula (I) may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 5.0 kg, and preferably between 0.5 kg and 4.0 kg of active material per hectare.

The compounds of formula (I) may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 1.0 kg and 20.0 kg, and preferably between 5.0 and 10.0 kg, of active material per hectare are particularly suitable for this purpose.

When used to control the growth of weeds by pre-emergence application, the compounds of formula (I) may be incorporated into the soil in which the weeds are expected to emerge. It will be appreciated that when the compounds of formula (I) are used to control the growth of weeds by post-emergence application, i.e. by application to the aerial or exposed portions of emerged weeds, the compounds of formula (I) will also normally come into contact with the soil and may also then exercise a pre-emergence control on later-germinating weeds in the soil.

Where especially prolonged weed control is required, the application of the compounds of formula (I) may be repeated if required.

According to a further feature of the present invention, there are provided herbicidal compositions comprising one or more of the isoxazole or 2-cyano-1,3-dione derivatives of formula (I) or agriculturally acceptable salts or metal complexes thereof, in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of formula (I)]. The term "homogeneously dispersed" is used to include compositions in which the compounds of formula (I) are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula (I).

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, talc, calcined magnesia, kieselguhr, tricalcium phosphate, powdered cork, absorbent carbon black and clays such as kaolin and bentonite. The solid compositions (which may take the form of dusts, granules or wettable powders) are preferably prepared by grinding the compounds of formula (I) with solid diluents or by impregnating the solid diluents or carriers with solutions of the compounds of formula (I) in volatile solvents, evaporating the solvents and, if necessary, grinding the products so as to obtain powders. Granular formulations may be prepared by absorbing the compounds of formula (I) (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of formula (I) may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Unless otherwise specified, the following percentages are by weight. Preferred herbicidal compositions according to the present invention are:

aqueous suspension concentrates which comprise from 10 to 70% of one or more compounds of formula (I), from 2 to 10% of surface-active agent, from 0.1 to 5% of thickener and from 15 to 87.9% of water;

wettable powders which comprise from 10 to 90% of one or more compounds of formula (I), from 2 to 10% of surface-active agent and from 8 to 88% of solid diluent or carrier;

water dispersible granules which comprise from 1 to 75%, e.g. 50 to 75%, of one or more compounds of formula (I), from 2 to 10% of surface-active agent and from 1 to 20%, e.g. 5–15%, of water soluble binder.

liquid emulsifiable suspension concentrates which comprise from 10 to 70% of one or more compounds of formula (I), from 5 to 15% of surface-active agent, from 0.1 to 5% of thickener and from 10 to 84.9% of organic solvent;

granules which comprise from 1 to 90%, e.g. 2 to 10% of one or more compounds of formula (I), from 0.5 to 7%, e.g. 0.5 to 2%, of surface-active agent and from 3 to 98.5%, e.g. 88 to 97.5%, of granular carrier and emulsifiable concentrates which comprise 0.05 to 90%, and preferably from 1 to 60% of one or more compounds of formula (I), from 0.01 to 10%, and preferably from 1 to 10%, of surface-active agent and from 9.99 to 99.94%, and preferably from 39 to 98.99%, of organic solvent.

Herbicidal compositions according to the present invention may also comprise the compounds of formula (I) in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine [2-chloro-4-ethylamino-6-isopropylamino-1,3,5-triazine], bromoxynil [3,5-dibromo-4-hydroxybenzonitrile], chlortoluron [N'-(3-chloro-4-methylphenyl)-N,N-dimethylurea], cyanazine [2-chloro-4-(1-cyano-1-methylethylamino)-6-ethylamino-1,3,5-triazine], 2,4-D [2,4-dichlorophenoxy-acetic acid], dicamba [3,6-dichloro-2-methoxybenzoic acid], acetochlor, difenzoquat [1,2-dimethyl-3,5-diphenyl-pyrazolium salts], flampropmethyl [methyl N-2-(N- benzoyl-3-chloro-4-fluoroanilino)-propionate], fluometuron [N'-(3-trifluoro- methylphenyl)-N,N-dimethylurea], isoproturon [N'-(4-isopropylphenyl)-N,N-dimethylurea], insecticides, e.g. synthetic pyrethroids, e.g. permethrin and cypermethrin, and fungicides, e.g. carbamates, e.g. methyl N-(1-butyl-carbamoyl-benzimidazol-2-yl)carbamate, and triazoles e.g. 1-(4-chlorophenoxy)-3,3-dimethyl-1-(1,2,4-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the isoxazole or 2-cyano-1,3-dione derivatives of formula (I) or, as is preferred, a herbicidal composition as hereinbefore described, and preferably a herbicidal concentrate which must be diluted before use, comprising at least one of the isoxazole or 2-cyano-1,3-dione derivatives of formula (I) within a container for the aforesaid derivative or derivatives of formula (I), or a said herbicidal composition, and instructions physically associated with the aforesaid container setting out the manner in which the aforesaid derivative or derivatives of formula (I) or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally lacquered, and plastics materials, bottles or glass and plastics materials and, when the contents of the container is a solid, for example granular, herbicidal compositions, boxes, for example of cardboard, plastics materials and metal, or sacks. The containers will normally be of sufficient capacity to contain amounts of the derivatives of formula (I) or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 20 kg of active material per hectare in the manner and for the purposes hereinbefore described.

The following Examples illustrate herbicidal compositions according to the present invention. The following are trade marks: Arylan; Synperonic; Arkopon; Sopropon; Tixosil; Soprophor; Ethylan; Attagel; Rhodorsil.

Example C1

An emulsifiable concentrate is formed from:

| | |
|---|---|
| Active ingredient (Compound 1) | 20% w/v |
| N-Methylpyrrolidone (NMP) | 25% w/v |
| Calcium dodecylbenzenesulphonate (CaDDBS) (Arylan CA) | 4% w/v |
| Nonylphenol ethylene oxide propylene oxide condensate (NPEOPO) (Synperonic NPE 1800) | 6% w/v |

Aromatic solvent (Solvesso) to 100 volumes by stirring NMP, active ingredient (Compound 1), CaDDBS, NPEOPO and 90% Aromatic solvent until a clear solution is formed, and adjusting to volume with Aromatic solvent.

Similar emulsifiable concentrates may be prepared by replacing Compound 1 with other compounds of formula (Ia), (Ib) or (Ic).

Example C2

A wettable powder is formed from:

| | |
|---|---|
| Active ingredient (Compound 1) | 50% w/w |
| Sodium dodecylbenzenesulphonate (Arylan SX85) | 3% w/w |
| Sodium methyl oleoyl taurate (Arkopon T) | 5% w/w |
| Sodium polycarboxylate (Sopropon T36) | 1% w/w |
| Microfine silicon dioxide (Tixosil 38) | 3% w/w |
| China clay | 38% w/w | by blending the above ingredients together and grinding the mixture in an air jet mill.

Similar wettable powders may be prepared by replacing Compound 1 with other compounds of formula (Ia), (Ib) or (Ic).

Example C3

A suspension concentrate is formed from:

| | |
|---|---|
| Active ingredient (Compound 1) | 50% w/v |
| Antifreeze (Propylene glycol) | 5% w/v |
| Ethoxylated tristyrylphenol phosphate (Soprophor FL) | 0.5% w/v |
| Nonyl phenol 9 mole ethoxylate (Ethylan BCP) | 0.5% w/v |
| Sodium polycarboxylate (Sopropon T36) | 0.2% w/v |
| Attaclay (Attagel) | 1.5% w/v |
| Antifoam (Rhodorsil AF426R) | 0.003% w/v |
| Water | to 100 volumes | by stirring the above ingredients together and milling in a bead mill.

Similar suspension concentrates may be prepared by replacing Compound 1 with other compounds of formula (Ia), (Ib) or (Ic).

Example C4

A water dispersible granule is formed from:

| | |
|---|---|
| Active ingredient (Compound 1) | 50% w/w |
| Sodium dodecylbenzenesulphonate (Arylan SX 85) | 3% w/w |
| Sodium methyl oleoyl taurate (Arkopon T) | 5% w/w |
| Sodium polycarboxylate (Sopropon T36) | 1% w/w |
| Binder (Sodium lignosulphonate) | 8% w/w |
| China clay | 30% w/w |
| Microfine silicon dioxide (Tixosil 38) | 3% w/w | by blending the above ingredients together, grinding the mixture in an air jet mill and granulating by addition of water in a suitable granulation plant (e.g. Fluid bed drier) and drying. Optionally the active ingredient may be ground either on its own or admixed with some or all of the other ingredients.

Similar water dispersible granules may be prepared by replacing Compound 1 with other compounds of formula (Ia), (Ib) or (Ic).

The compounds of the invention have been used in herbicidal applications according to the following procedures.

METHOD OF USE OF HERBICIDAL COMPOUNDS:

a) General

Appropriate quantities of the compounds used to treat the plants were dissolved in acetone to give solutions equivalent to application rates of up to 100 g test compound per hectare (g/ha). These solutions were applied from a standard laboratory herbicide sprayer delivering the equivalent of 290 liters of spray fluid per hectare.

b) Weed control: Pre-emergence

The seeds were sown in 70 mm square, 75 mm deep plastic pots in non-sterile soil. The quantities of seed per pot were as follows:

| Weed species | Approx number of seeds/pot |
|---|---|
| 1) Broad-leafed weeds | |
| Abutilon theophrasti | 10 |
| Amaranthus retroflexus | 20 |
| Galium aparine | 10 |
| Ipomoea purpurea | 10 |
| Sinapis arvensis | 15 |
| Xanthium strumarium | 2 |
| 2) Grass weeds | |
| Alopecurus myosuroides | 15 |
| Avena fatua | 10 |
| Echinochloa crus-galli | 15 |
| Setaria viridis | 20 |
| 3) Sedges | |
| Cyperus esculentus | 3 |
| Crop | |
| 1) Broad-leafed | |
| Cotton | 3 |
| Soya | 3 |
| 2) Grass | |
| Maize | 2 |
| Rice | 6 |
| Wheat | 6 |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed control: Post-emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

| Weed species | No. of plants per pot | Growth stage |
|---|---|---|
| 1) Broad leafed weeds | | |
| Abutilon theophrasti | 3 | 1–2 leaves |
| Amaranthus retroflexus | 4 | 1–2 leaves |
| Galium aparine | 3 | 1st whorl |
| Ipomoea purpurea | 3 | 1–2 leaves |
| Sinapis arvensis | 4 | 2 leaves |
| Xanthium strumarium | 1 | 2–3 leaves |
| 2) Grass weeds | | |
| Alopecurus myosuroides | 8–12 | 1–2 leaves |
| Avena fatua | 12–18 | 1–2 leaves |
| Echinochloa crus-galli | 4 | 2–3 leaves |
| Setaria viridis | 15–25 | 1–2 leaves |
| 3) Sedges | | |
| Cyperus esculentus | 3 | 3 leaves |
| 1) Broad leafed Crops | | |
| Cotton | 2 | 1 leaf |
| Soya | 2 | 2 leaves |
| 2) Grass Crops | | |
| Maize | 2 | 2–3 leaves |
| Rice | 4 | 2–3 leaves |
| Wheat | 5 | 2–3 leaves |

The compounds used to treat the plants were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20–24 days after spraying. The results were expressed as the percentage reduction in growth or damage to the crop or weeds, in comparison with the plants in the control pots.

When applied post-emergence at 100 g/ha or less compounds 1–7 and 110–115 gave at least 90% reduction in growth of one or more of the weed species.

When applied pre-emergence at 1000 g/ha or less compounds 1–7 and 110–115 gave at least 70% reduction in growth of one or more of the weed species.

At levels of application toxic to the weeds these compounds were selective in at least one of the crop species.

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A compound having the formula:

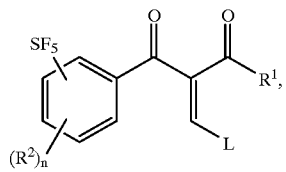
(II)

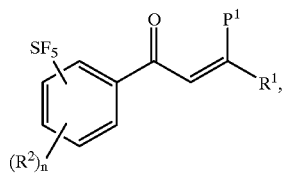
(IV)

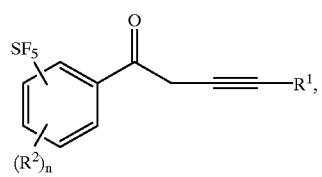
(V)

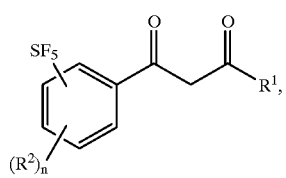
(VI)

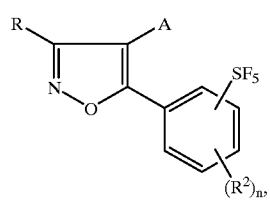
(VII)

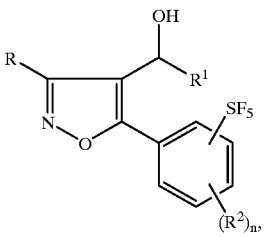
(VIII)

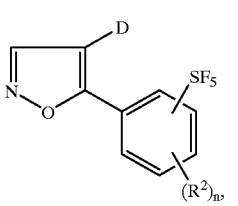
(IX)

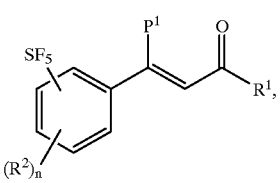
(X)

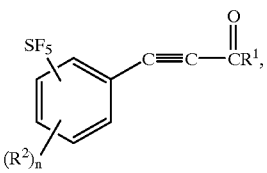
(XI)

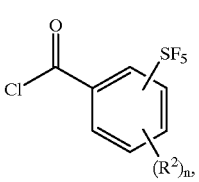
(XII)

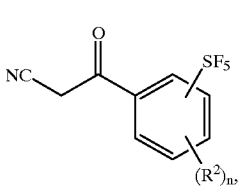
(XIV)

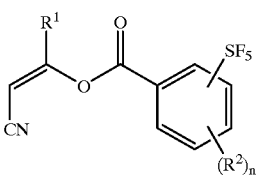
(XV)

-continued

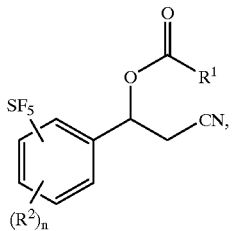
(XVI)

wherein:

R is hydrogen or —$CO_2R^3$;

$R^1$ is:
  straight- or branched-chain alkyl having up to six carbon atoms which is unsubstituted or is substituted by one or more halogen; or
  cycloalkyl having from three to six ring carbon atoms which is unsubstituted or is substituted by one or more substituents selected from the group consisting of $R^4$ and halogen;

$R^2$ is:
  halogen;
  straight- or branched-chain alkyl having up to six carbon atoms which is substituted by one or more —$OR^5$;
  cycloalkyl having from three to six carbon atoms; or
  a member selected from the group consisting of nitro, cyano, —$CO_2R^5$, —$NR^5R^6$, —$S(O)_pR^7$, —$O(CH_2)_mOR^5$, —$COR^5$, —$N(R^8)SO_2R^7$, —$OR^7$, —OH, —$OSO_2R^7$, —$(CR^9R^{10})_tSO_qR^{7a}$, —$CONR^5R^6$, —$N(R^8)$—$C(Z)$=Y, —$(CR^9R^{10})NR^8R^{11}$ and $R^4$;

n is zero or an integer from one to three; when n is greater than one, then the groups $R^2$ are the same or different;

m is one, two or three;

p is zero, one or two;

q is zero, one or two;

t is an integer from one to four;

$R^3$ is:
  straight- or branched-chain alkyl having up to six carbon atoms which is unsubstituted or is substituted by one or more substituents selected from the group consisting of halogen, —OR, —$CO_2R^5$, —$S(O)_pR^7$, phenyl and cyano; or
  phenyl which is unsubstituted or is substituted by one or more substituents selected from the group consisting of halogen, —$OR^5$ and $R^4$;

$R^4$ is straight- or branched-chain alky, alkenyl or alkynyl having up to six carbon atoms which is unsubstituted or is substituted by one or more halogen;

$R^5$ and $R^6$, which are the same or different, are each hydrogen or $R^4$;

$R^7$ and $R^{7a}$ independently are $R^4$, cycloalkyl having from three to six ring carbon atoms, or —$(CH_2)_w$-phenyl wherein phenyl is unsubstituted or is substituted by from one to five $R^{12}$ which are the same or different;

w is zero or one;

$R^8$ is:
  hydrogen;
  straight- or branched-chain allyl, alkenyl or alkynyl having up to ten carbon atoms which is unsubstituted or is substituted by one or more halogen;
  cycloalkyl having from three to six ring carbon atoms;
  —$(CH_2)_w$-phenyl wherein phenyl is unsubstituted or is substituted by from one to five $R^{12}$ which are the same or different; or
  $OR^{13}$;

$R^9$ and $R^{10}$ independently are hydrogen or straight- or branched-chain alkyl having up to six carbon atoms which is unsubstituted or is substituted by one or more halogen;

$R^{11}$ is —$S(O)_qR^7$ or —$C(Z)$=Y;

$R^{12}$ is:
  halogen;
  straight- or branched-chain alkyl having up to three carbon atoms which is unsubstituted or is substituted by one or more halogen; or
  a member selected from the group consisting of nitro, cyano, —$S(O)_pR^3$ and —$OR^5$;

Y is oxygen or sulphur;

Z is , —$NR^8R^{13}$, —$NR^8$—$NR^{13}R^{14}$, —$SR^7$ or —$OR^7$;

$R^{13}$ and $R^{14}$ independently are $R^8$;

L is a leaving group;

$P^1$ is a leaving group;

A is a halogen atom; and

D is a carboxy group, a carboxylic acid chloride, a carboxylic ester or a cyano group; or a compound having the formula

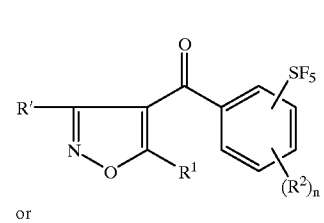
(Ia')

or

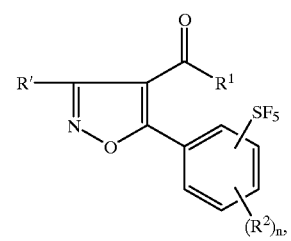
(Ib')

wherein $R^1$, $R^2$ and n are as defined above and R' is an amnide or nitrile group.

2. A compound according to claim 1, wherein the 2-position of the phenyl group is substituted.

3. A compound according to claim 1, wherein the 5- and 6-positions of the phenyl group are unsubstituted.

4. A compound according to claim 1, wherein $R^1$ is:
  straight- or branched-chain alkyl having up to three carbon atoms which is unsubstituted or is substituted by one or more halogen; or
  cyclopropyl or 1-methylcyclopropyl.

5. A compound according to claim 4, wherein $R^1$ is cyclopropyl.

6. A compound according to claim 1, wherein $R^2$ is:
  halogen;
  straight- or branched-chain alkyl or alkenyl having up to four carbon atoms which is unsubstituted or is substituted by one or more halogen;

or a member selected from the group consisting of nitro, cyano, —S(O)$_p$R$^7$, —OR$^7$ and —CR$^9$R$^{10}$SO$_q$R$^7$.

7. A compound according to claim 1, wherein n is zero, one or two.

8. A compound according to claim 1, wherein R$^3$ is straight- or branched-chain alkyl having up to six carbon atoms which is unsubstituted or is substituted by one or more halogen.

9. A compound according to claim 1, having at least one substituent selected from the group consisting of:

R is hydrogen or —CO$_2$R$^3$;

R$^1$ is cyclopropyl or 1-methylcyclopropyl;

R$^2$ is halogen or straight- or branched-chain alkyl having up to three carbon atoms which is unsubstituted or is substituted by one or more halogen, or R$^2$ is —S(O)$_p$R$^7$ or —CH$_2$S(O)$_q$R$^{7a}$;

R$^3$ is straight- or branched-chain alkyl having from one to three carbon atoms;

R$^7$ is methyl or ethyl which is unsubstituted or is substituted by one or more halogen; and R$^{7a}$ is straight- or branched-chain alkyl having up to four carbon atoms which is unsubstituted or is substituted by one or more halogen, or R$^{7a}$ is phenyl which is unsubstituted or is substituted by one or more halogen or —S(O) R$^7$.

* * * * *